(12) United States Patent
Shippy, III et al.

(10) Patent No.: US 7,927,362 B2
(45) Date of Patent: Apr. 19, 2011

(54) LASER ABLATED ELASTOMER SHEATH PROFILES TO ENABLES STENT SECUREMENT

(75) Inventors: James Lee Shippy, III, Roswell, GA (US); Karl Alan Jagger, Deephaven, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1089 days.

(21) Appl. No.: 11/186,370

(22) Filed: Jul. 21, 2005

(65) Prior Publication Data

US 2007/0021817 A1 Jan. 25, 2007

(51) Int. Cl.
*A61F 2/06* (2006.01)
(52) U.S. Cl. .................................. 623/1.11
(58) Field of Classification Search ........... 623/1.11, 623/1.15, 1.18, 1.37, 1.12, 1.23; 606/108
See application file for complete search history.

(56) References Cited

U.S. PATENT DOCUMENTS

| | | | |
|---|---|---|---|
| 2,701,559 A | 2/1955 | Cooper | |
| 5,653,690 A * | 8/1997 | Booth et al. | 604/103.07 |
| 5,681,345 A * | 10/1997 | Euteneuer | 623/1.11 |
| 5,788,707 A * | 8/1998 | Del Toro et al. | 606/108 |
| 5,826,588 A * | 10/1998 | Forman | 128/898 |
| 5,968,069 A * | 10/1999 | Dusbabek et al. | 606/194 |
| 6,066,155 A * | 5/2000 | Amann et al. | 606/192 |
| 6,096,045 A * | 8/2000 | Del Toro et al. | 606/108 |
| 6,221,097 B1 * | 4/2001 | Wang et al. | 623/1.11 |
| 6,254,608 B1 | 7/2001 | Solar | 606/108 |
| 6,258,099 B1 * | 7/2001 | Mareiro et al. | 606/108 |
| 6,331,186 B1 * | 12/2001 | Wang et al. | 623/1.11 |
| 6,342,066 B1 * | 1/2002 | Toro et al. | 623/1.11 |
| 6,350,277 B1 * | 2/2002 | Kocur | 623/1.11 |
| 6,443,880 B2 * | 9/2002 | Blais et al. | 492/16 |
| 6,478,814 B2 * | 11/2002 | Wang et al. | 623/1.12 |
| 2004/0106977 A1 * | 6/2004 | Sullivan et al. | 623/1.12 |
| 2004/0172119 A1 * | 9/2004 | Eidenschink | 606/194 |
| 2004/0172121 A1 * | 9/2004 | Eidenschink et al. | 623/1.11 |

FOREIGN PATENT DOCUMENTS

| | | |
|---|---|---|
| EP | 0 783 897 A2 | 7/1997 |
| EP | 0834293 A1 | 4/1998 |
| EP | 1 382 367 A1 | 1/2004 |
| WO | 95-33422 | 12/1995 |
| WO | 98/14233 | 4/1998 |
| WO | 02/24115 A2 | 3/2002 |
| WO | 03/024362 A1 | 3/2003 |
| WO | 2004/075792 A1 | 9/2004 |
| WO | 2004/098696 A1 | 11/2004 |

OTHER PUBLICATIONS

U.S. Appl. No. 10/747,546, Eidenschink, et al.*
U.S. Appl. No. 10/757,646, Weber, et al.*
U.S. Appl. No. 10/784,337, Eidenschink, et al.*

* cited by examiner

*Primary Examiner* — Todd E Manahan
*Assistant Examiner* — Jonathan A Hollm
(74) *Attorney, Agent, or Firm* — Vidas, Arrett & Steinkraus (57) ABSTRACT

The stent placement dilation balloon assembly comprises a catheter having a distal end, a distal end portion, and a proximal end, a balloon mounted to, about, and around the distal end portion of the catheter. The assembly further includes an elastic sheath positioned about and around the balloon. The outer surface of the sheath includes a profile which encourages stent securement. A stent is mounted on the sleeve for placement in a vessel in a human body.

7 Claims, 12 Drawing Sheets

LASER ABLATED ELASTOMER SHEATH PROFILES TO ENABLES STENT SECUREMENT

FIELD OF THE INVENTION

This invention relates to an assembly and method for delivering and deploying an expandable medical device, particularly within a lumen of a body vessel. More specifically, this invention relates to stent securement devices, most notably, sheaths positioned between the balloon and the stent.

BACKGROUND OF THE INVENTION

Percutaneous transluminal coronary angioplasty (PTCA) is a procedure that is well established for the treatment of blockages, lesions, stenosis, thrombus, etc. present in body lumens such as the coronary arteries and/or other vessels.

A widely used form of percutaneous coronary angioplasty makes use of a dilatation balloon catheter, which is introduced into and advanced, through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. No. 5,681,345; U.S. Pat. No. 5,788,707; U.S. Pat. No. 5,968,069; U.S. Pat. No. 6,066,155; U.S. Pat. No. 6,096,045; U.S. Pat. No. 6,221,097; U.S. Pat. No. 6,331,186; U.S. Pat. No. 6,342,066; U.S. Pat. No. 6,350,277; U.S. Pat. No. 6,443,880; and U.S. Pat. No. 6,478,814.

It is desirous to provide for a stent delivery system which has the capability to both deliver and seat a stent, while also providing the catheter with a desired low profile prior to delivery.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is particularly concerned with stent securement and the delivery and deployment of expandable stents. Some embodiments of the invention are directed to catheters and catheter assemblies having an expandable medical balloon mounted on its distal end. An elastic sheath is positioned about the expandable medical balloon and an expandable medical device, such as a stent, is mounted onto the sheath. The outer surface of the sheath includes a securement mechanism, which engages the loaded stent.

In at least one embodiment, the outer surface of the sheath includes a plurality of notches, which are cut into the sheath. The notches are cut at an angle, such that circumferential blades are formed. The blades may engage the loaded stent, providing axial securement.

In at least one embodiment, the outer surface of the sheath includes a plurality of circumferential ribs. The ribs may be integral with the sheath material or be bonded to the sheath. The ribs may engage the loaded stent, providing axial securement. In some embodiments the stent securement mechanism(s) minimize or eliminate axial movement of the stent while permitting rotational movement of the stent about the sheath.

In at least one embodiment, the outer surface of the sheath includes stent retention strips or patches. The strips or patches may engage the loaded stent, providing axial and/or circumferential securement. The sheath may also have memory characteristics, such that, when it is in its relaxed state, it takes on an accordion configuration. A relaxed state is the state that the sheath is in when there are no external forces on sheath other than ambient forces. When in its accordion configuration, the stent retention strips or patches are predominately exposed relative to the outer surface of sheath which is not covered with strips or patches.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Figure 1:
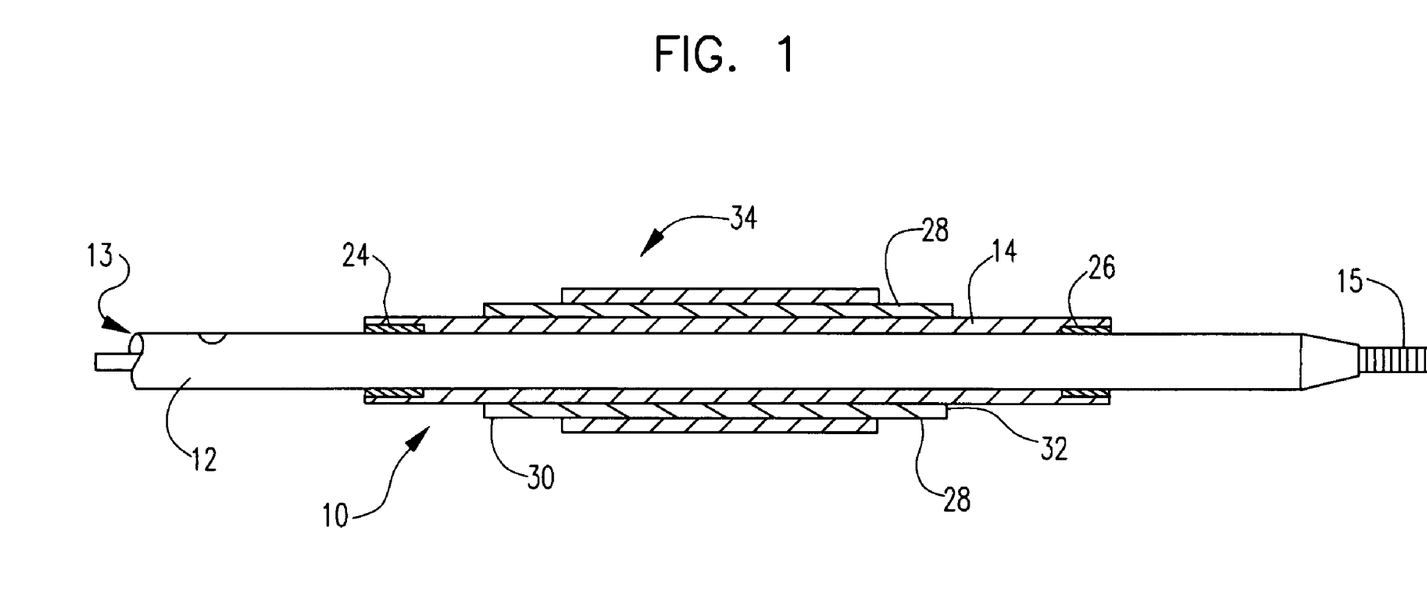
FIG. 1 shows a partial cross-sectional view of an embodiment of the invention.
Figure 2:
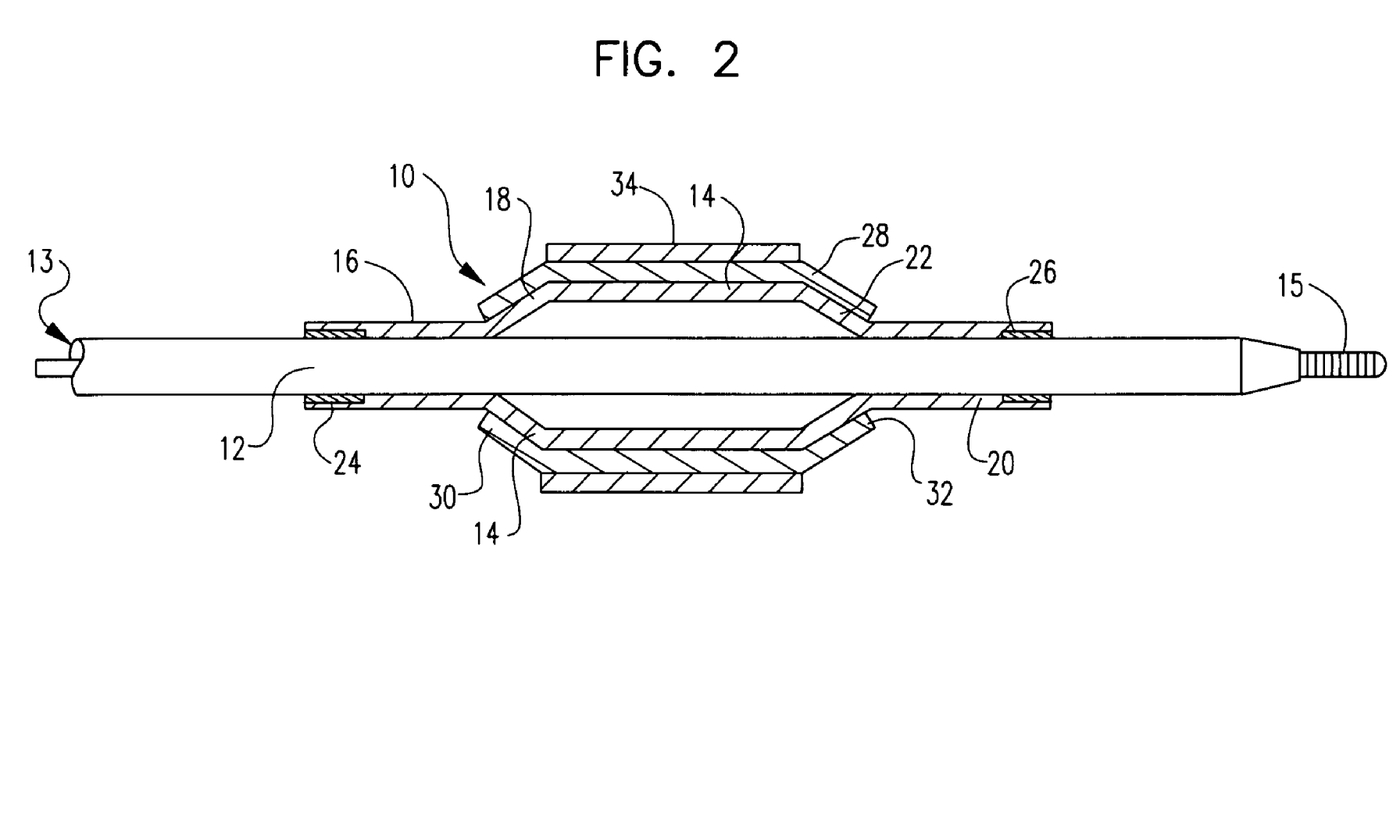
FIG. 2 shows a partial cross-sectional view of an embodiment of the invention.

In at least one embodiment of the invention, an example of which is shown in FIGS. 1-2, the distal end portion 10 of a catheter assembly is shown. The distal end portion 10 includes a catheter shaft 12 and a medical balloon 14 mounted thereon. FIG. 1 illustrates the medical balloon 14 in its contracted state and FIG. 2 illustrates the medical balloon 14 in its expanded state. As shown in FIG. 2, the medical balloon 14 has a proximal waist 16 and cone 18 and a distal waist 20 and cone 22. The waists 16, 20, of the medical balloon 14 are bonded to the catheter shaft 12 at points 24 and 26 via adhesion, chemical and/or thermal welding, mechanical engagement, etc.

It should be understood that the present invention contemplates using other balloon mounted catheter configurations, as well as folding balloons, which are well known in the art. The workings of such balloon catheters are well known in the art.

As shown in FIGS. 1-2, a sheath 28 is situated about the medical balloon 14. The sheath 28 has a proximal end 30 and a distal end 32. A stent 34 is, in turn, mounted onto the sheath 28. The sheath 28 may vary in length. It may be as long as the stent 34, shorter than the stent 34 or it may extend over the cones 18, 22, or the waists 16, 20.

The sheath 28 has elastic characteristics allowing it to expand with the medical balloon 14 as the balloon 14 is expanded, typically under pressure. The sheath 28 conforms in its relaxed state to the balloon 14 in its contracted state. When the internal balloon pressure is reduced after expansion of the balloon 14, the constricting elastic sheath 28 collapses the balloon to a reduced profile.

The sheath 28 may be made by conventional means, including extrusion. Suitable sheath 28 materials include, but not limited to, bio-compatible materials having elastic properties suitable for conformance and function. The sheath 28 is thin and may have a thickness range from 0.001" to 0.002".

Figure 3:
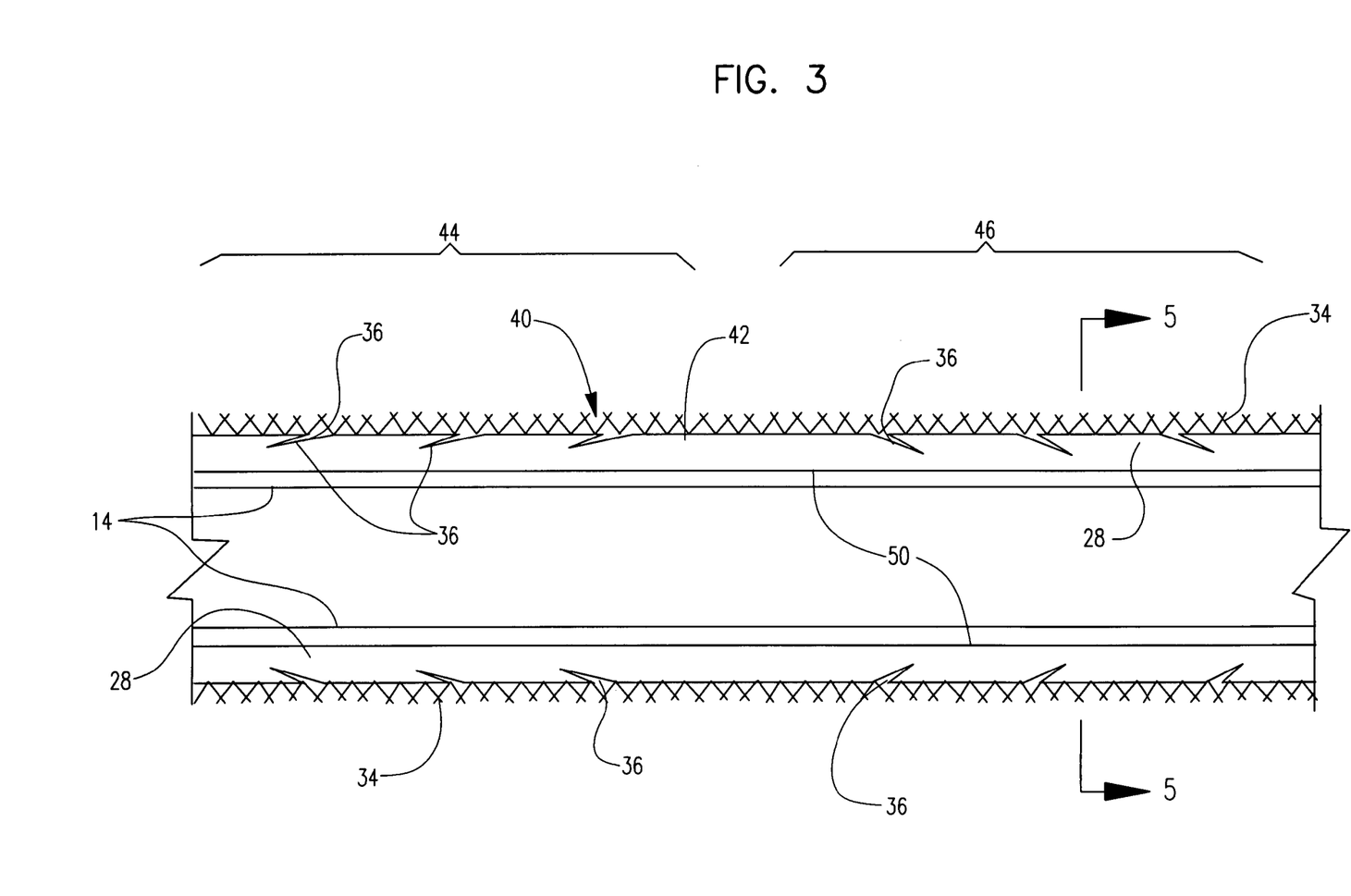
FIG. 3 shows a cross-sectional view of an embodiment of the sheath of the present invention.
Figure 4:
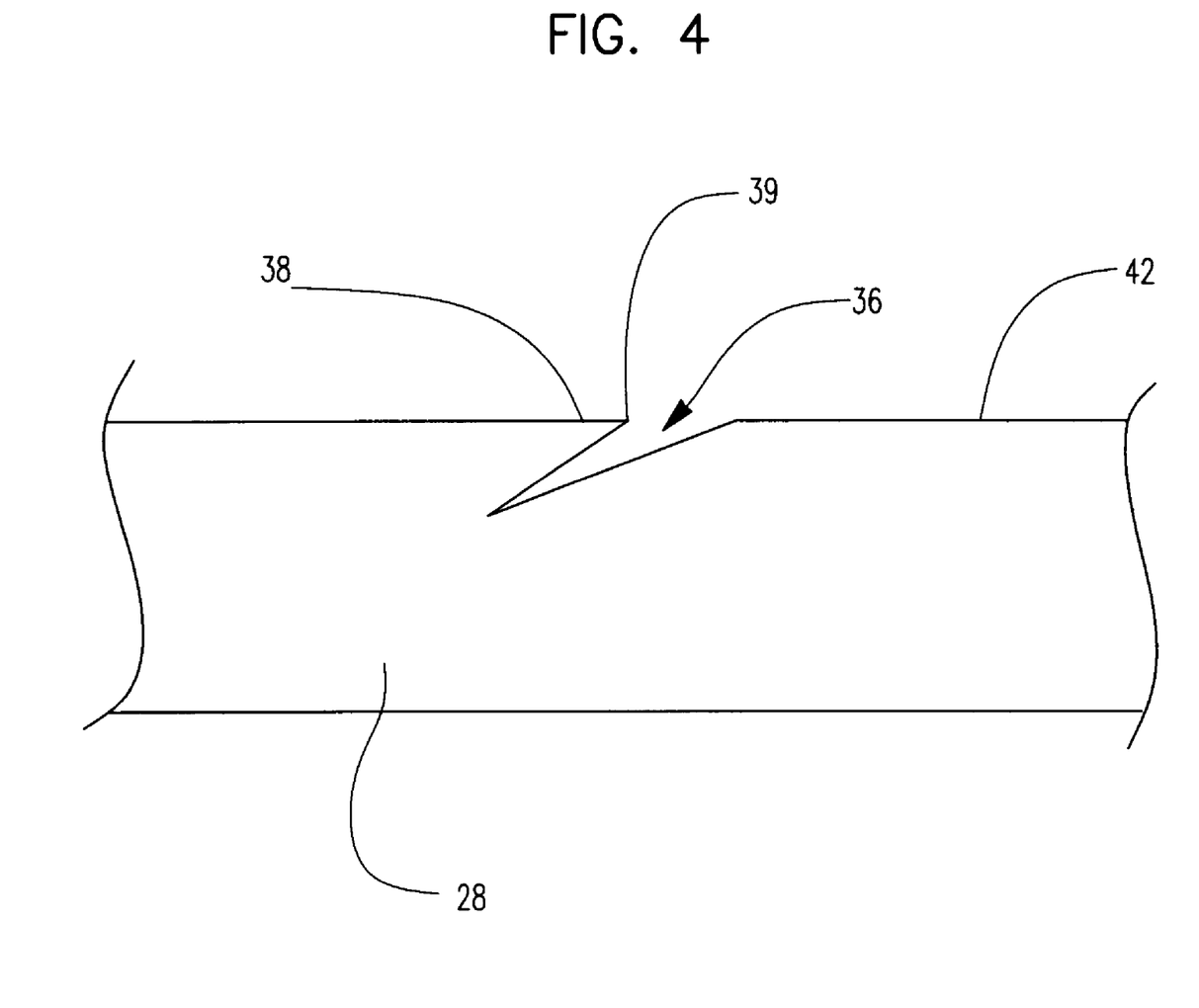
FIG. 4 shows a cross-sectional view of a portion of an embodiment of the sheath of the present invention.

FIG. 3 shows a longitudinal cross-section of the sheath 28 with a stent 34 mounted thereon. In one particular embodiment, as shown, the sheath 28 has notches 36 in its outer surface. As shown in FIG. 4, the notches 36 may be cut into the sheath 28 at an angle relative to a radial notch, which would be a notch which is cut at a perpendicular angle relative to the outer surface 42 of the sheath 28, such that a blade 38 is produced. As can be seen, the blade 38 has a barb-like cross-sectional profile terminating in an edge 39. This edge 39 engages struts or cross sections of a stent. As shown at point 40, the blades 38 may engage the mounted stent 34.

The notches 36 may be created via conventional mechanical means or by an ablation process, such as, but not limited to, UV laser ablation and chemical etching. Some examples of the use of laser ablation in the area of medical devices such as catheters are shown and described in U.S. Pat. No. 5,826,588, the entire content of which is incorporated herein by reference.

The present invention also contemplates methods of imparting various profiles and patterns into sheaths 28 via ablation to provide stent securement. The outer surface of the sheath 28 may be selectively textured to provide various patterns of notches and/or bumps. The sheath 28 may be ablated prior to mounting it on the catheter or after it has been mounted.

In the design shown, axial stent securement is provided by the engagement between the stent 34 and the notches 36, but circumferential rotation is permitted, in this particular embodiment, due to the circumferential symmetry of the notches 36 around the sheath 28.

The notches 36 may be circumferentially situated around the sheath 28 and may be randomly or uniformly spaced on the length of the sheath 28. The angle of the notches 28 may be unidirectional, such that the blades 38 are pointing in the same direction relative to the outer surface 42 of the sheath 28. The blades 38 may also be multidirectional in a random fashion or in a patterned or uniform fashion. FIG. 3 illustrates a configuration, wherein a plurality of blades 38 are directed in a first direction 44 and a plurality of blades 38 are directed in a second direction 46, wherein the first 44 and second 46 directions are opposingly oriented relative to a plane which is perpendicular to the outer surface 42 of the sheath 28. FIG. 3 shows a sheath 28 with three blades 38, 44, pointing in one direction and three blades 38, 46, pointing in an opposing direction. It should be understood that the angle between the first direction and the perpendicular plane and the angle between the second direction and the perpendicular plane may not be equal. It should also be understood that the blades 44, 46, may also extend in directions which are away from one another. It also should be understood that the notches may be cut in a very shallow fashion, such that the blades are flaps pointing down the length of the sheath.

Figure 5:
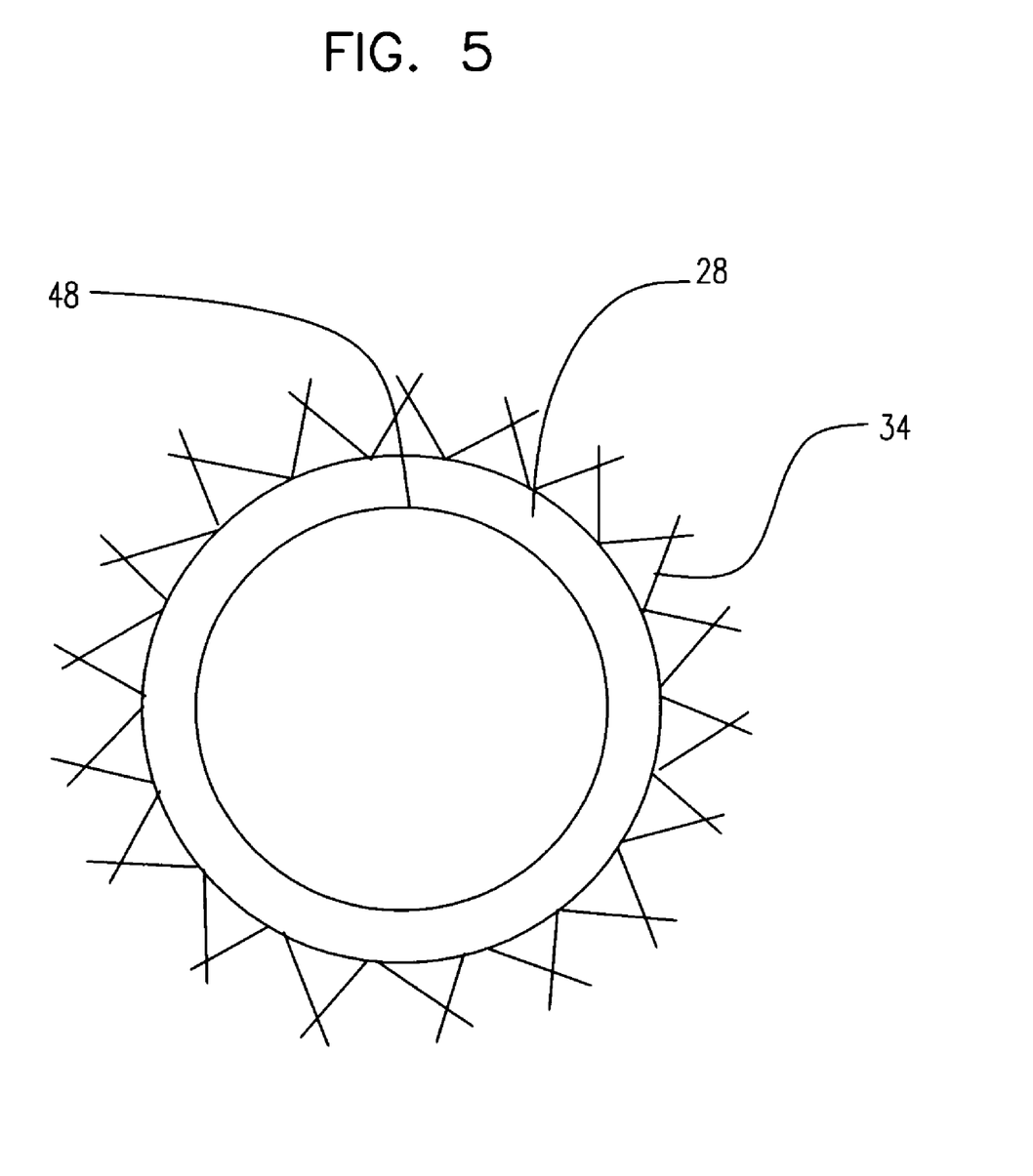
FIG. 5 shows a cross-sectional view of the embodiment of FIG. 3 along lines 5-5.

FIG. 5 shows a cross-sectional view of the embodiment shown in FIG. 3 along lines 5-5. In an embodiment of invention, the sheath 28 may have a seam 48 at least partly or entirely along its length. The seam 48 is used to secure the sheath 28 to the balloon 14. If desired, the longitudinal seam 48 may connect the sheath to the balloon 14 to prevent the sheath 28 and stent 34 from rotating about the balloon 14 and prevent the sheath 28 and stent 34 from slipping along the length of the balloon 14. However, the sheath 28 and stent 24 may remain unattached to the balloon 14 so they may rotate around the balloon.

The inner surface 50 of the sheath 28 in the various embodiments disclosed herein may be coated with a hydrophilic and/or lubricious coating in order to reduce or limit friction between the sheath 28 and the balloon 14, as the balloon expands or contracts. The sheath 28 may also be affixed to the balloon 14 along longitudinal lines or points to prevent axial slippage of the sheath 28 over the balloon 14. The connection between the sheath 28 and the balloon may be achieved via adhesion, welding, intentional lack of lubricant, exposure to heat, moisture, pressure changes or ETO sterilization to selective portions, etc.

Figure 6:
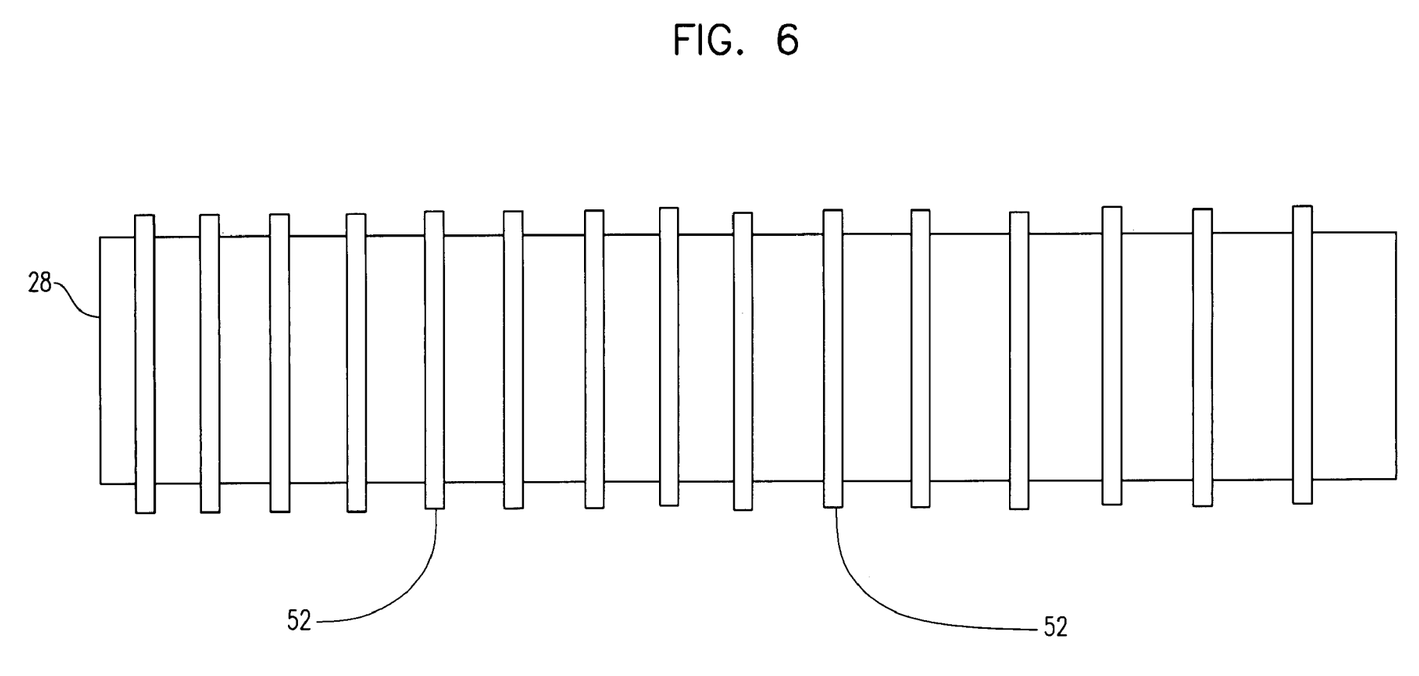
FIG. 6 shows a side view of an embodiment of the sheath of the present invention.
Figure 7:
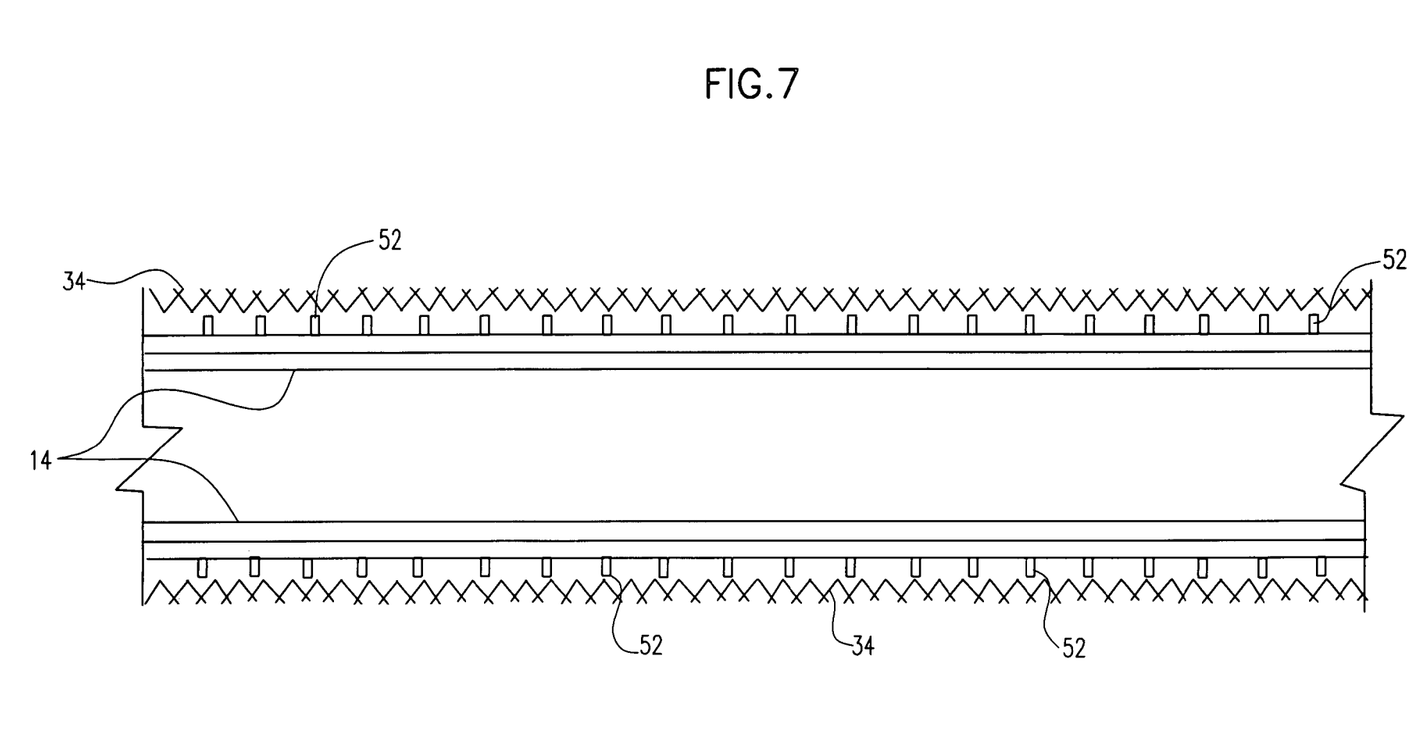
FIG. 7 shows a cross-sectional view of an embodiment of the sheath of the present invention.

FIGS. 6-7 illustrate a further embodiment of an alternative external sheath 28 profile. FIG. 6 shows a side view of the sheath 28 and FIG. 7 shows a cross-sectional view of the sheath 28 about a balloon 14 with a stent 34 mounted thereon. In this particular embodiment, the sheath 28 has circumferential ribs 52 longitudinally spaced along the length of the sheath 28. The spacing may be uniform, patterned or random. As with the embodiment shown in FIG. 3, the ribs may be fully or partially circumferential and may be integral with the sheath 28 material. The ribs 52 engage the stent 34 and provide resistance to axial movement, while allowing circumferential or rotational movement of the stent.

Providing the catheter assembly with a sheath 28, which allows the stent 34 to readily or freely rotate thereabout is of particular usefulness in assemblies wherein the stent is deployed at a bifurcation of vessels. By providing a mechanism whereby the stent is rotatable about the sheath prior to deployment, allows the assembly, using a variety of techniques, to rotationally align a side branch opening of the stent with a side branch vessel.

Examples of stent delivery systems that illustrates the benefits of such rotatability for the delivery of stent to a vessel bifurcation are shown and described in:

U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each of which are incorporated herein by reference.

Embodiments of the present invention can be incorporated into those shown and described in the various references cited above. Likewise, embodiments of the inventions shown and described therein can be incorporated herein.

In the embodiments shown in FIGS. 6-7, the ribs 52 may be formed from a piece of tubing via conventional mechanical means or by an ablation process, such as, but not limited to, UV laser ablation or chemical etching. The ribs 52 may also be elastic rings bonded to the sheath 28 or take the form of a build up of adhesive. The ribs 52 of the embodiments may also be coated with an adhesive or a tacky substance.

FIGS. 8-12 illustrate a further embodiment of the invention. In the embodiments shown, the sheath 28 includes stent retention strips or patches 56, 58, to aid in securement of the stent 34, when the stent 34 is crimped onto the sheath 28. The stent retention strips or patches 56, 58, are positioned on the sheath such that, when the balloon 14, sheath 28 and stent 34 are expanded, the relative stent retention area decreases and enables the stent 34 to be deployed.

Figure 8:
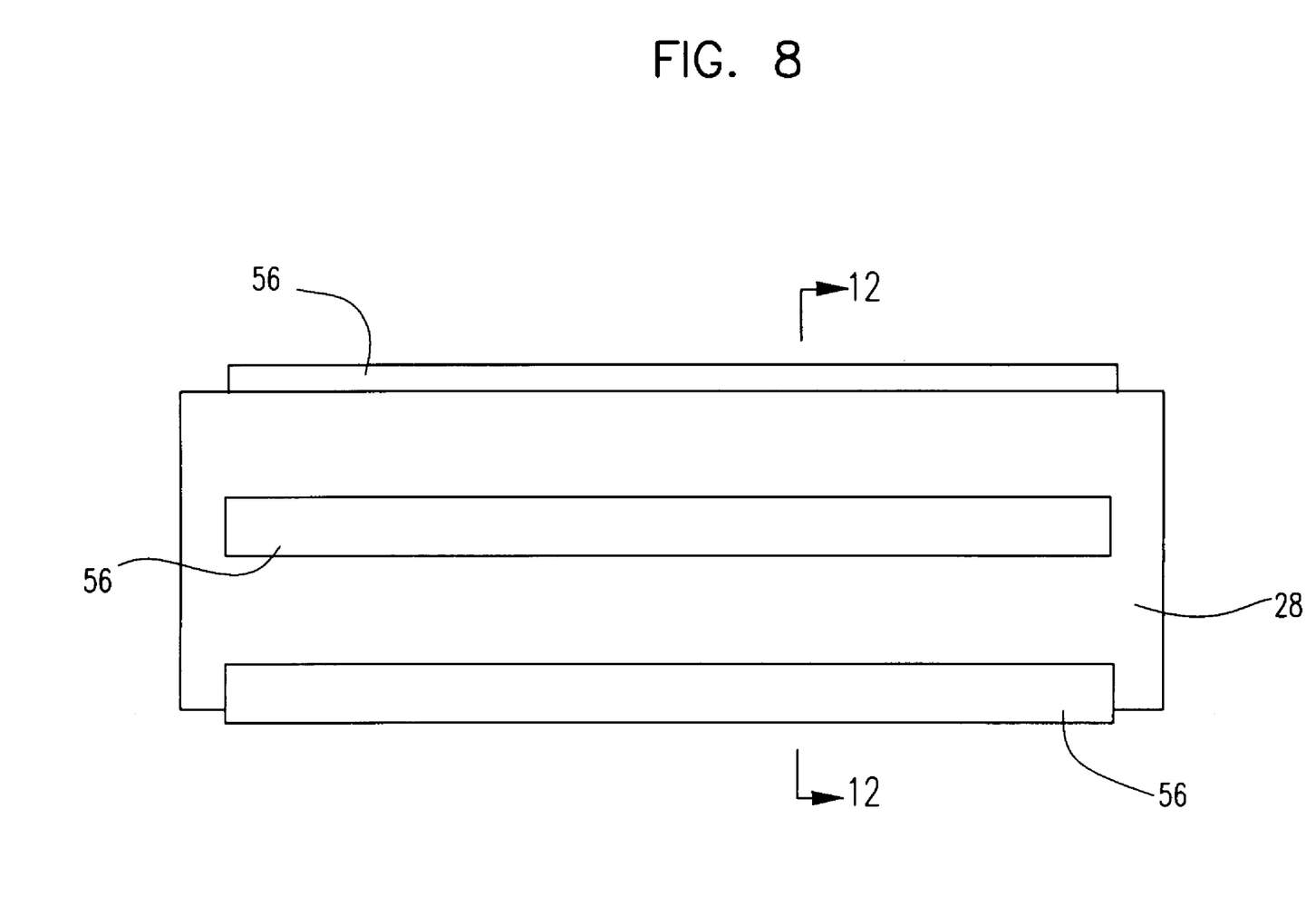
FIG. 8 shows a side view of an embodiment of the sheath of the present invention.
Figure 9:
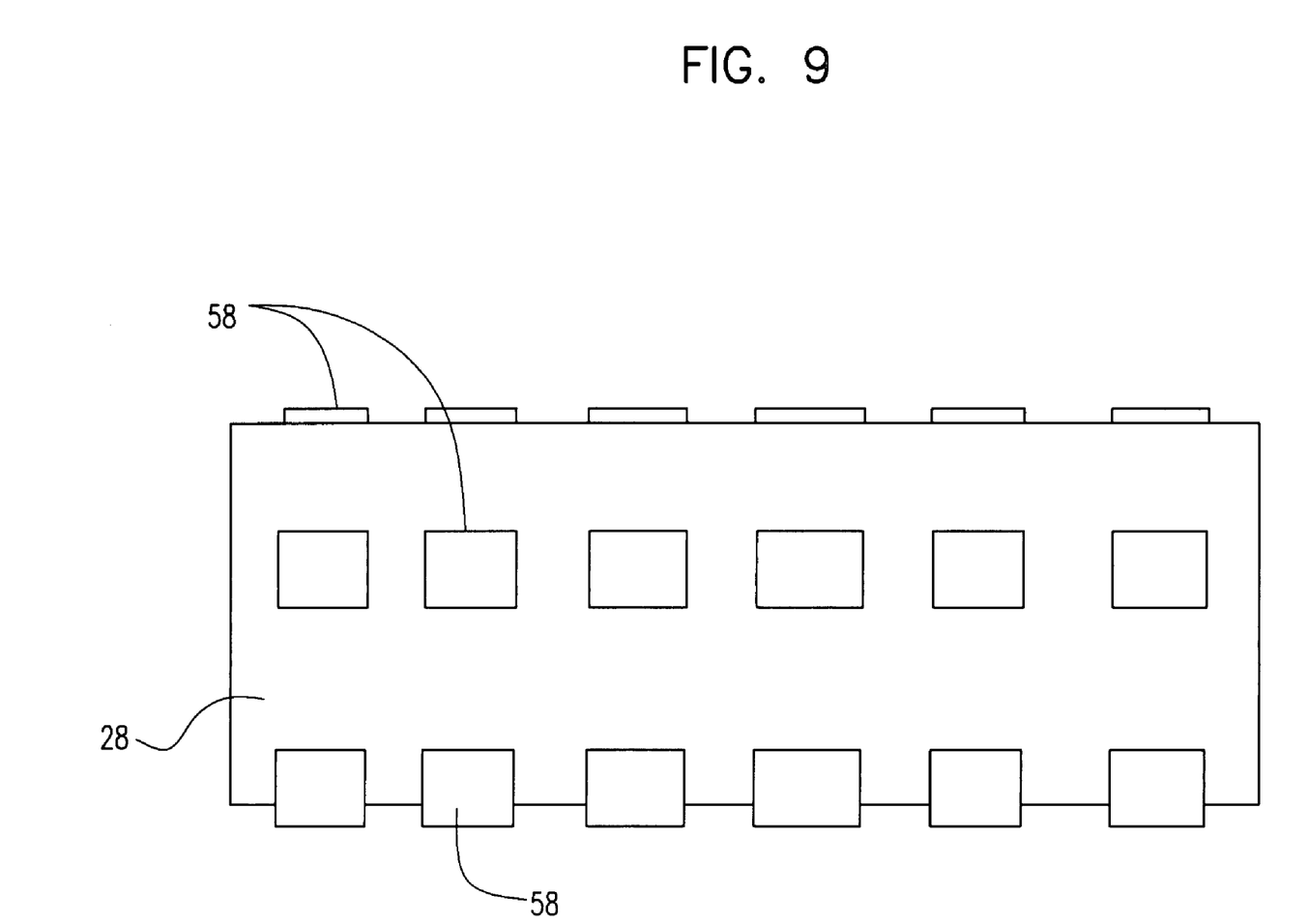
FIG. 9 shows a side view of an embodiment of the sheath of the present invention.
Figure 10:
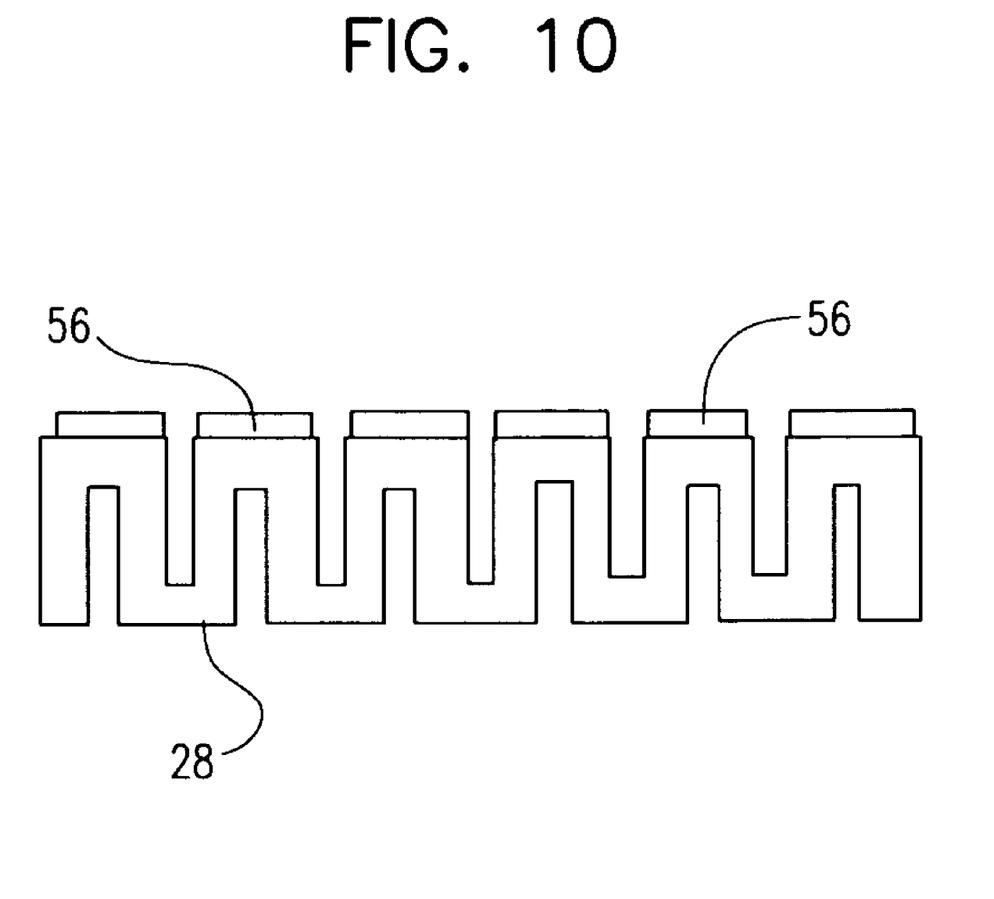
FIG. 10 shows a cross-sectional view of a portion of an embodiment of the sheath of the present invention.

FIGS. 8-9 and 10 show the sheath 28 in its expanded, tubular form. That being the shape the sheath 28 takes when the balloon 14 is in its expanded state. The sheath 28 may have a plurality of stent retention strips 56 longitudinally aligned along the length of the sheath 28. As can be seen in FIG. 9, the stent retention strip 56 may be replaced with isolated patches 58. The stent retention strips 56 or patches 58 are surfaces which have a higher coefficient of friction relative to the remaining surface. This textured surface may be imparted on the sheath 28 via the application of adhesive, selective grinding, roughening or scoring, including surface scoring via laser ablation, etc.

Figure 11:
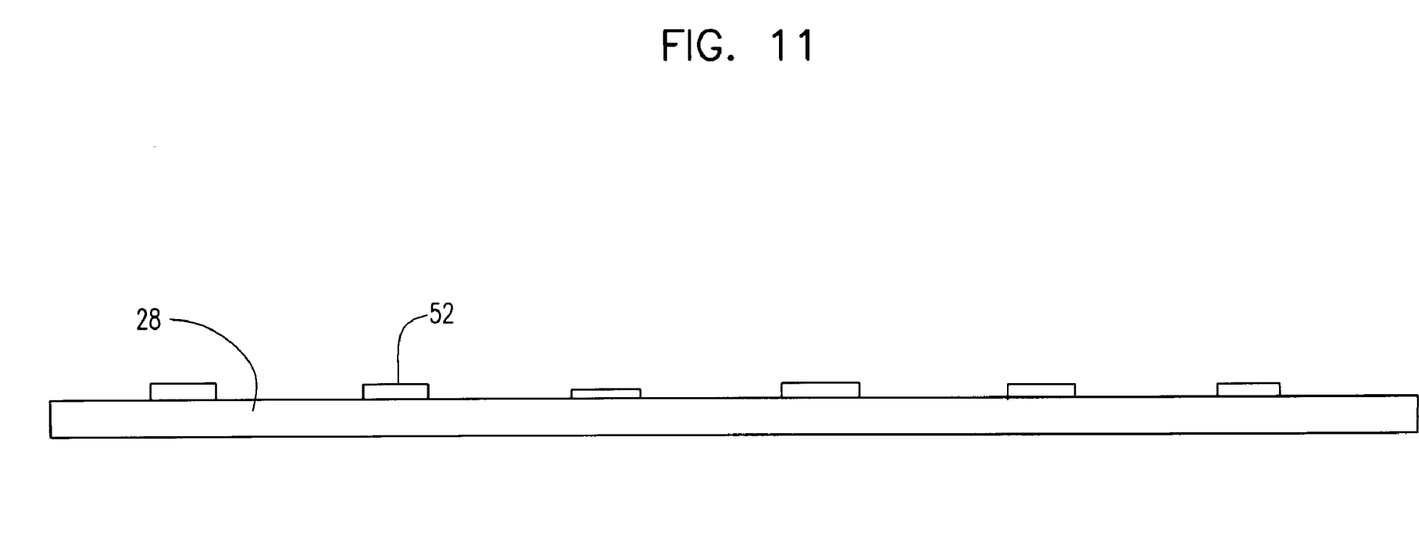
FIG. 11 shows a cross-sectional view of a portion of an embodiment of the sheath of the present invention.
Figure 12:
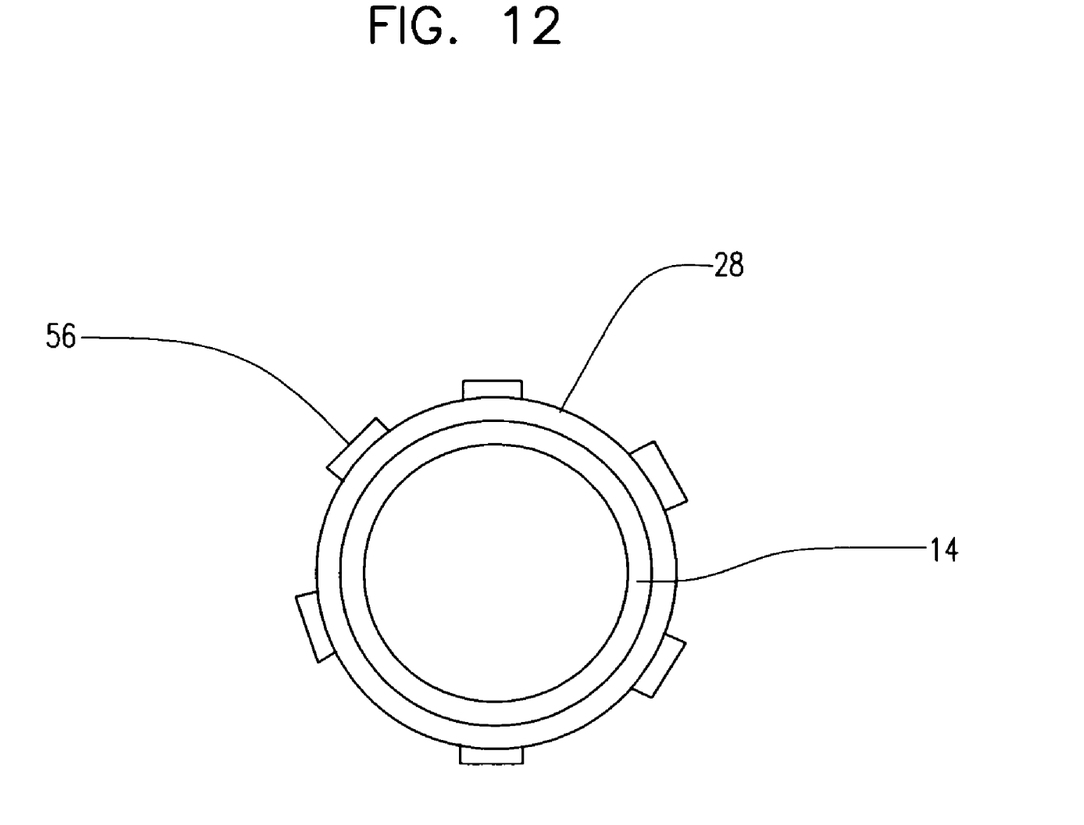
FIG. 12 shows a cross-sectional view of the embodiment of FIG. 8 along lines 12-12.

FIGS. 10-11 show a flat cross-sectional profile of the sheath shown in FIG. 8. In these figures, the sheath 28, as shown in FIG. 8, is unwrapped from its tubular shape and flattened out. As shown in FIG. 10, when the sheath 28 is in its relaxed state, it takes on an accordion profile. FIG. 11 shows the sheath when it's stretched out. In the accordion configuration, the stent retention strips 56 are prominently exposed on the outer side, which would be exposed to the stent 34. When the sheath 28 is wrapped around and attached to the balloon 14 when it is in its contracted state, the outer exposed surface of the sheath 28 is dominated by the stent retention strips 56 so as to provide greater securement for the mounted stent 34. When the balloon 14 is expanded, the sheath 28 is stretched out, losing its accordion configuration, as shown in FIG. 12. The accordion shape may be created through precision mechanical mass removal, laser ablation, controlled compression or buckling of the polymer tube after mass removal, etc.

Balloon 14 may be a typical angioplasty, stent delivery balloon or other inflatable member which may be used or incorporated into a catheter assembly. The balloon 16 may be constructed of any suitable balloon material known to those of skill in the art. Commonly employed materials include the thermoplastic elastomeric and non-elastomeric polymers and the thermosets including the moisture curable polymers. Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, polytetraflouroethylene, copolymers thereof, and mixtures thereof. Some of these classes are available both as thermosets and as thermoplastic polymers.

In some embodiments the stent or other portion of the assembly, including the sheath 28, may include one or more areas, bands, coatings, members, etc. that is (are) detectable by imaging modalities such as X-Ray, MRI or ultrasound. In some embodiments at least a portion of the stent, sheath and/or adjacent assembly is at least partially radiopaque.

In the various embodiments described herein, the catheter assembly 10 may be a fixed wire catheter or any other catheter design. In the embodiment depicted in FIGS. 1 and 2, for example, the catheter 10 is an over the wire design, wherein the catheter shaft 12 defines a primary guidewire lumen 13 along which a primary guidewire 15 may be advanced.

In operation, the guidewire 15 of the present invention is initially advanced through a vessel to a target location. By advancing the catheter assembly 10 along the guidewire 15, the stent 34 carrying balloon 14 is positioned at the target site. Once the stent 34 is delivered, the balloon 16 is deflated and the assembly is withdrawn from the vessel.

A therapeutic agent may be placed on the stent 34 and/or the sheath 28 in the form of a coating. Often the coating includes at least one therapeutic agent and at least one polymer. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above materials throughout the application are intended for illustrative purposes only, and not as a limitation on the scope of the present invention. Suitable polymeric materials available for use are vast and are too numerous to be listed herein and are known to those of ordinary skill in the art.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
a catheter, the catheter having a proximal portion and a distal portion;
a medical balloon coaxially mounted on the distal portion of the catheter, the medical balloon comprising a proximal waist, a proximal cone, a distal waist, a distal cone and a body portion, wherein the body portion is positioned between the proximal and distal cones, the balloon having a reduced diameter state and an expanded diameter state;
a sheath, the sheath being tubular and being coaxially mounted about at least a portion of the body portion of the medical balloon, wherein the sheath comprises a tubular body and is elastic, such that it stretches with the medical balloon as the balloon is expanded from its reduced diameter state to its expanded diameter state, the sheath having an inner surface and an outer surface and comprising a plurality of ribs radially extending from the outer surface, each rib extending in a circumferential direction completely around the sheath; and
a medical device mounted about the sheath, the medical device having a reduced diameter configuration and an expanded diameter configuration.

2. The catheter assembly of claim 1, wherein the medical device is a single luminal stent or a bifurcated stent.

3. The catheter assembly of claim 1, wherein the ribs prevent axial movement of the medical device, but allow circumferential movement.

4. The catheter assembly of claim 2, wherein the medical device is a bifurcated stent, the catheter assembly being arranged and constructed, such that the bifurcated stent may be manually rotated about the catheter, when the bifurcated stent is in reduced diameter configuration.

5. The catheter assembly of claim 4, wherein the catheter assembly is constructed and arranged, such that the sheath is rotatable.

6. The catheter assembly of claim 4, wherein the catheter assembly is constructed and arranged, such that the stent is rotatable about the sheath.

7. The catheter assembly of claim 1, wherein the sheath is fixed relative to the medical balloon.

* * * * *